US012146870B1

(12) United States Patent
Speck et al.

(10) Patent No.: US 12,146,870 B1
(45) Date of Patent: Nov. 19, 2024

(54) CALIBRATION OF HUMIDITY AND METHANE INSIDE GAS SENSOR HOUSING

(71) Applicant: Schlumberger Technology Corporation, Sugar Land, TX (US)

(72) Inventors: Andrew J. Speck, Cambridge, MA (US); Aditi Chakrabarti, Cambridge, MA (US); Mathieu Dauphin, Cambridge, MA (US); Albert Ballard Andrews, Cambridge, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 18/650,878

(22) Filed: Apr. 30, 2024

(51) Int. Cl.
*G01N 33/00* (2006.01)
(52) U.S. Cl.
CPC ..... *G01N 33/0006* (2013.01); *G01N 33/0014* (2013.01)
(58) Field of Classification Search
None
See application file for complete search history.

(56) References Cited

U.S. PATENT DOCUMENTS

| 11,320,335 B2* | 5/2022 | Ghasemvand | G01M 3/223 |
| 11,549,924 B2* | 1/2023 | Tao | G01K 13/00 |
| 2013/0289899 A1* | 10/2013 | Tolton | G01M 3/38 |
| | | | 702/51 |
| 2021/0239667 A1* | 8/2021 | Gentner | G01N 35/00693 |
| 2022/0357232 A1* | 11/2022 | Brandt | G01M 3/04 |

FOREIGN PATENT DOCUMENTS

| WO | 2023215173 A1 | 11/2023 |
| WO | 2024030525 A1 | 2/2024 |
| WO | 2024059020 A1 | 3/2024 |

* cited by examiner

*Primary Examiner* — Peter J Macchiarolo
*Assistant Examiner* — Jermaine L Jenkins

(57) ABSTRACT

Systems and methods are described for developing a model to predict humidity (relative, absolute) values inside a closed housing with an absorbent filter. In an example, a methane sensor that includes an internal atmospheric sensor and an external atmospheric sensor can be placed at a site. A computing device can use measurements from the atmospheric sensors to calculate predicted relative and absolute humidity values inside the methane sensor. The computing device can train a gaussian process regression model to calibrate sensor data based on the external temperature and humidity. When the model predicts the ambient methane within a predetermined degree of allowance, the model can be applied to live readings from methane sensors in the field.

20 Claims, 4 Drawing Sheets

CALIBRATION OF HUMIDITY AND METHANE INSIDE GAS SENSOR HOUSING

BACKGROUND

Methane is the main component of natural gas and is a much more potent greenhouse gas than carbon dioxide with a global warming potential of 50 times that of carbon dioxide. Oil and gas facilities emit methane either due to planned flaring or venting to enable safe operations or as a result of unplanned fugitive leaks. Continuous monitoring of methane emissions by sensors installed permanently in client locations provides a cost-effective and sensitive way to detect these emissions from multiple locations and field sites.

Some methane monitoring point instruments have been developed that are sensitive, quantitative, accurate and inexpensive, and have been deployed in the field to detect methane leaks from oil and gas facilities. Some such instruments include a sensing component that is made of a metal oxide, which is embedded in a sensor housing that has a protective filter that prevents interfering gases and moisture from entering the housing. Metal oxide sensors are sensitive to temperature and humidity changes inside the sensor housing. However, as the ambient air diffuses into the gas sensor cavity via an absorbent filter, it slows down the humidity equilibration inside the housing, which makes the calibration of the sensor challenging.

Current methane point instruments cannot directly measure temperature and humidity values inside the housing. Humidity inside the sensor housing is a critical parameter for calibrating metal oxide sensors and estimating the correct concentrations of methane in the environment. Additionally, absorbent filters delay the equilibration of the humidity inside the housing with the outside humidity.

As a result, a need exists for determining interior humidity of a sensor with a closed housing.

SUMMARY

Examples described herein include systems and methods for accurately determining the humidity inside a sensor housing protected by an absorbent filter based on measured values of external relative humidity and temperature.

This invention describes methods to infer the humidity values (both relative and absolute) inside the sensor housing by knowing only the outdoor measured values of temperature and relative humidity via an atmospheric sensor. A computing device can generate a calibration model using iterative measurements taken both inside and outside the sensor housing. For example, to train the model, a methane sensor can be used that has atmospheric sensors on both the inside and outside of the sensor housing. The atmospheric sensors can iteratively measure the ambient temperature and relative humidity and send the measurements to a computing device.

The computing device can use the temperature and humidity measurements to create a calibration model that can be applied to methane sensor measurements. To create the calibration model, the computing device can receive iterative temperature and relative humidity measurements from both the internal and external sensors. For each measurement received, the computing device can calculate predicted relative and absolute humidity values for inside the sensor. The computing device can save these predicted values in arrays.

The computing device can apply a regression model to the arrays, such as a gaussian process regression model. The computing device can then test the model against additional temperature and humidity measurements at the site. The computing device can modify the model until the measured values match the predicted values within a predetermined degree of allowance.

After the model for the site is created, the computing device can apply the model to sensor readings from methane sensors that do not have an internal atmospheric sensor. This is because the model allows the computing device to determine the relative and absolute humidity inside the sensor by applying the calibration model to readings received from an external atmospheric sensor.

Both the foregoing general description and the following detailed description are exemplary and explanatory only and are not restrictive of the examples, as claimed.

DESCRIPTION OF THE EXAMPLES

Reference will now be made in detail to the present examples, including examples illustrated in the accompanying drawings. Wherever possible, the same reference numbers will be used throughout the drawings to refer to the same or like parts.

Systems and methods are described for developing a model to predict humidity (relative, absolute) values inside a closed housing with an absorbent filter. In an example, a methane sensor that includes an internal atmospheric sensor and an external atmospheric sensor can be placed at a site. A computing device can use measurements from the atmospheric sensors to calculate predicted relative and absolute humidity values inside the methane sensor. The computing device can train a gaussian process regression model to calibrate sensor data based on the external temperature and humidity. When the model predicts the ambient methane within a predetermined degree of allowance, the model can be applied to live readings from methane sensors in the field.

Figure 1:
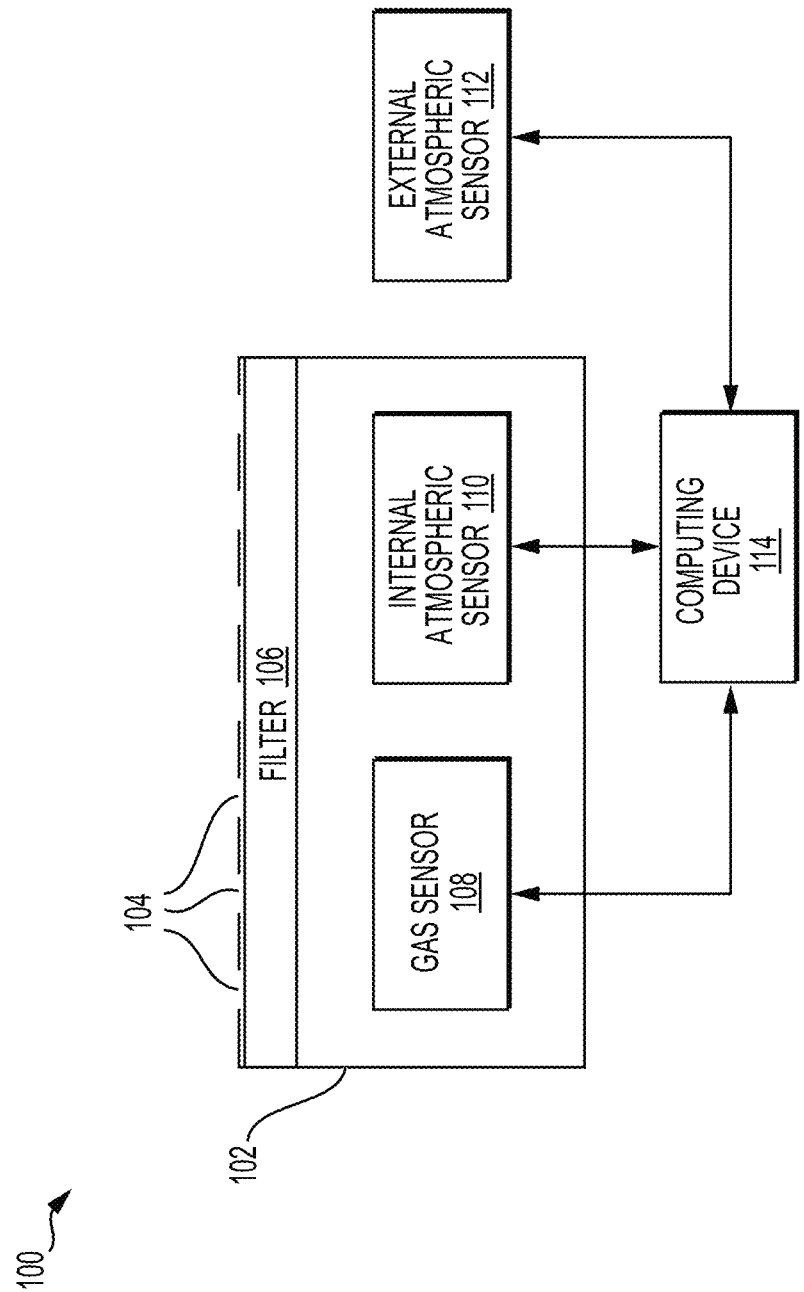
FIG. 1 is an illustration of an example methane sensor.

FIG. 1 is an illustration of an example methane sensor device 100. The methane sensor device 100 can include a housing 102 that houses internal components. The housing 102 can be made of any material that particles in the air cannot penetrate. For example, the housing 102 can be made of a solid plastic or metal. The housing 102 can include slits 104. The slits 104 can be openings through which ambient air can enter the housing 102. A filter 106 can be positioned adjacent to the slits 104 so that any air particles entering the housing 102 must pass through the filter 106 to reach other internal components of the methane sensor device 100. The filter 106 can be made of an absorbent material that prevents interfering gases and moisture from entering the housing 102. The filter 106 helps reduce atmospheric fluctuations inside the methane sensor device 100 and reduce interference from non-methane gases.

A gas sensor 108 can be positioned within the housing 102 on the internal side of the filter 106. The gas sensor 108 can be a sensor device that can measure methane levels. The gas sensor 108 can be an electrochemical sensor that oxidizes, or reduces, ambient methane at an electrode to produce a current. This current can be used to determine the gas concentration. In an example, the gas sensor 108 can be made of a metal oxide. Metal oxide is sensitive to temperature and humidity changes inside the sensor housing. Knowing the temperature and humidity inside the housing 102 is required to accurately calibrate the gas sensor 108 because the ambient temperature and humidity affect how quickly the methane gas oxidizes the gas sensor 108.

The methane sensor device 100 can include an internal atmospheric sensor 110 that can measure the temperature, relative humidity, and absolute humidity inside the methane sensor device 100. Relative humidity indicates the actual water content of air as a percentage of the maximum amount it could possibly hold. Absolute humidity describes the actual amount of water vapor in the air. The internal atmospheric sensor 110 can be a physical or virtual sensor. A physical sensor can be a physical device that measures the actual temperature, relative humidity, and absolute humidity. The measurements can then be used to calibrate the gas sensor 108.

A virtual sensor can be a device that estimates the temperature, relative humidity, and absolute humidity based on a model. The virtual sensor can use various inputs to estimate the internal temperature, relative humidity, and absolute humidity, such as the temperature, relative humidity, and absolute humidity outside the methane sensor device 100. These external measurements can be recorded by an external atmospheric sensor 112. The external atmospheric sensor 112 can be any kind of sensor capable of measuring ambient temperature and humidity.

The gas sensor 108 and atmospheric sensors 110, 112 can transmit their measurements to a computing device 114. The computing device 114 can be one or more processor-based devices, such as a server, personal computer, tablet, or cell phone. The computing device 114 can include a software application (not shown) that can receive and interpret sensor measurements received from the gas sensor 108 and atmospheric sensors 110, 112. The computing device 114 can create a calibration model to calculate and predict humidity levels inside the methane sensor 108 based on measurements received from the gas sensor 108 and atmospheric sensors 110, 112. The gas sensor 108 and atmospheric sensors 110, 112 can communicate with the computing device 114 using any appropriate communication means, such as through a hardwired or a wireless connection. For example, the gas sensor 108 and atmospheric sensors 110, 112 can communicate their measurements to the computing device 114 using BLUETOOTH or WIFI.

Figure 2:
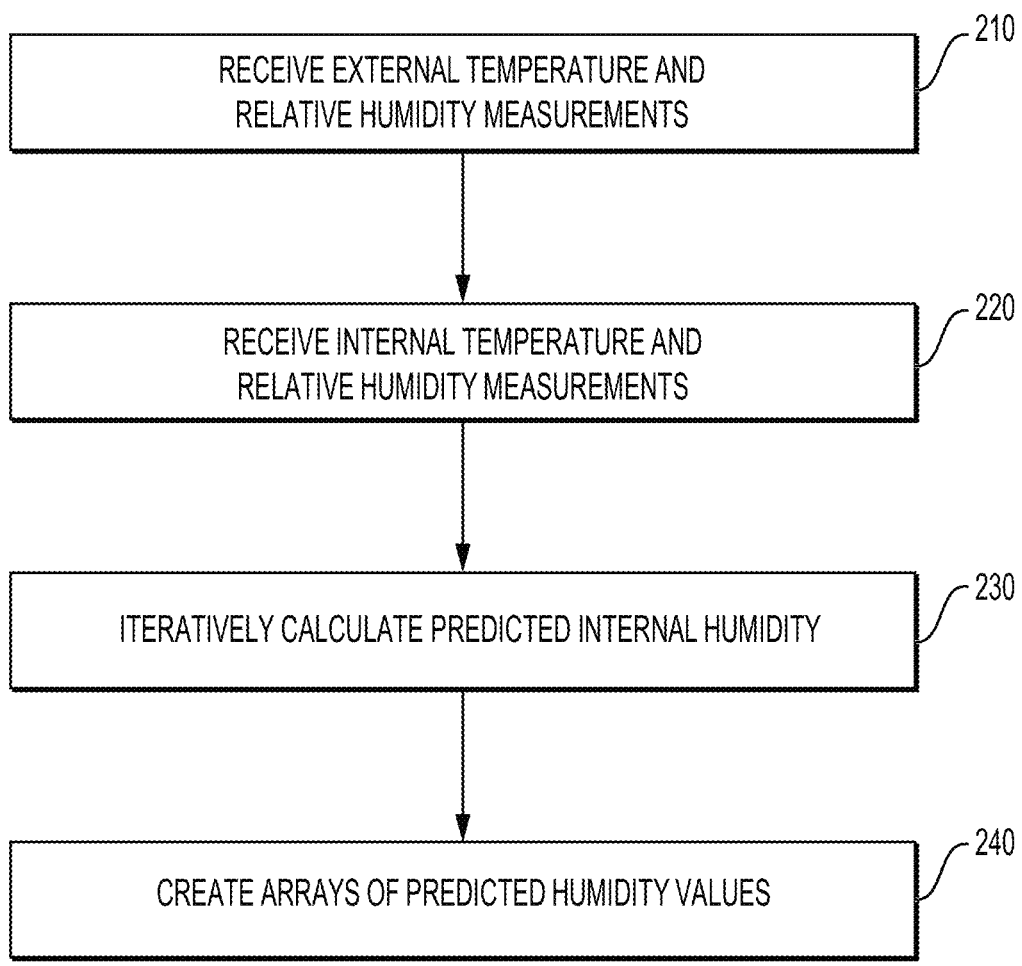
FIG. 2 is a flowchart of an example method for developing a model to predict humidity values inside a closed housing with an absorbent filter.

FIG. 2 is a flowchart of an example method for developing a model to predict humidity (relative, absolute) values inside a closed housing with an absorbent filter. At stage 210, the computing device 114 can receive the external temperature and humidity measurements from the external atmospheric sensor 112. The measured humidity can be the relative humidity. The external temperature and humidity measurements can be of ambient temperature and humidity outside the methane sensor housing 102.

The external atmospheric sensor 112 can take the measurements and send them to the computing device 114. The external atmospheric sensor 112 can send the measurements using any available communication protocol. For example, the external atmospheric sensor 112 can send the measurements through a hardwired connection. In another example, the external atmospheric sensor 112 can be equipped with a wireless transmitter that sends the measurements to the computing device 114 wirelessly.

At stage 220, the computing device 114 can receive the internal temperature and humidity measurements from the internal atmospheric sensor 110. Like the external atmospheric sensor 112, the internal atmospheric sensor 110 can send the measurements using a hardwired or wireless connection. In an example, the methane sensor 108 used for developing the model can include an internal atmospheric sensor 110, but other sensors can be used at a site that do not include an internal atmospheric sensor 110. For example, the methane sensor device 100 with an internal atmospheric sensor 110 can be used to develop a calibration model that can be applied to external temperature and humidity measurements from other sensors to predict their internal temperature and humidity.

At stage 230, the computing device 114 can iteratively calculate the internal relative humidity over a period of time. Table 1 below includes the example calculations made to determine the predicted internal relative humidity in the methane sensor device 100 based on the external temperature and humidity. In Table 1 below AHe represents the external absolute humidity, AHi represents the absolute internal humidity, Te represents the external temperature, RHe represents the external relative humidity, RHi represents the internal relative humidity, ΔT represents the difference between the measured internal and external temperatures, RHip represents the predicted internal relative humidity, and AHip represents the predicted internal absolute humidity. A and B are fitting coefficients that can be used to calibrate the model based on temperature and humidity measurements taken inside the sensor 100.

TABLE 1

AHe = f(Te, RHe)
AHi = f(Te, RHi)
δ = (A + Te)(AHi − AHe) + (B + Te) ΔT
RHip = RHi + δ
AHip = f(Te, RHip)
RHi = RHip

In the above calculations, the computing device 114 can first calculate AHe and AHi. This can be done using the standard equations for calculating AH. The computing device 114 can then calculate δ using the AHe and AHi values. δ is an adjustment equation added to RHi to calculate RHip. The Te and RHip can then be inserted into the AH equation to obtain the AHip. The RHip can then be assumed to be the RHi.

The computing device 114 can calculate new RHip and AHip values as the ambient conditions change. For example, the computing device 114 can be configured to calculate new RHip and AHip values each time the temperature or RHe changes by a predetermined amount, such as one degree Celsius in temperature or one percentage point of RHe.

In an example, as the computing device 114 calculates more AHip and RHip values, the computing device 114 can adjust the A and B fitting coefficients to fine tune the model. For example, where the AHip and RHip values do not match their corresponding measured AHi and RHi values, the computing device 114 can adjust the A and B fitting coefficients so that all the measured and predicted internal AH and RH values more closely match.

At stage 240, the computing device 114 can create one or more arrays of AHip and RHip values based on the Te and RHe values. As an example, the computing device 114 can maintain one array for RHe and another for AHip. The arrays can have Te values as column headers and RHe values as row headers. Each time the computing device 114 calculates new RHip and AHip values, the computing device 114 can insert those into a field in the array that match the corresponding Te and RHe values.

In an example, the arrays can be used to calibrate measurements received from the gas sensor 108. For example, one methane sensor device 100 with an internal atmospheric sensor 110 can be used to take actual RHi and Ti measurements, and those measurements can be used with RHe and Te measurements taken from the external atmospheric sensor 112 to build the RHip and AHip arrays. Other methane sensors 100 that do not have an internal atmospheric sensor 110 can be placed at the site. The computing device 114 can instead use the RHip and AHip arrays to calibrate readings from the gas sensors 108.

Figure 3:
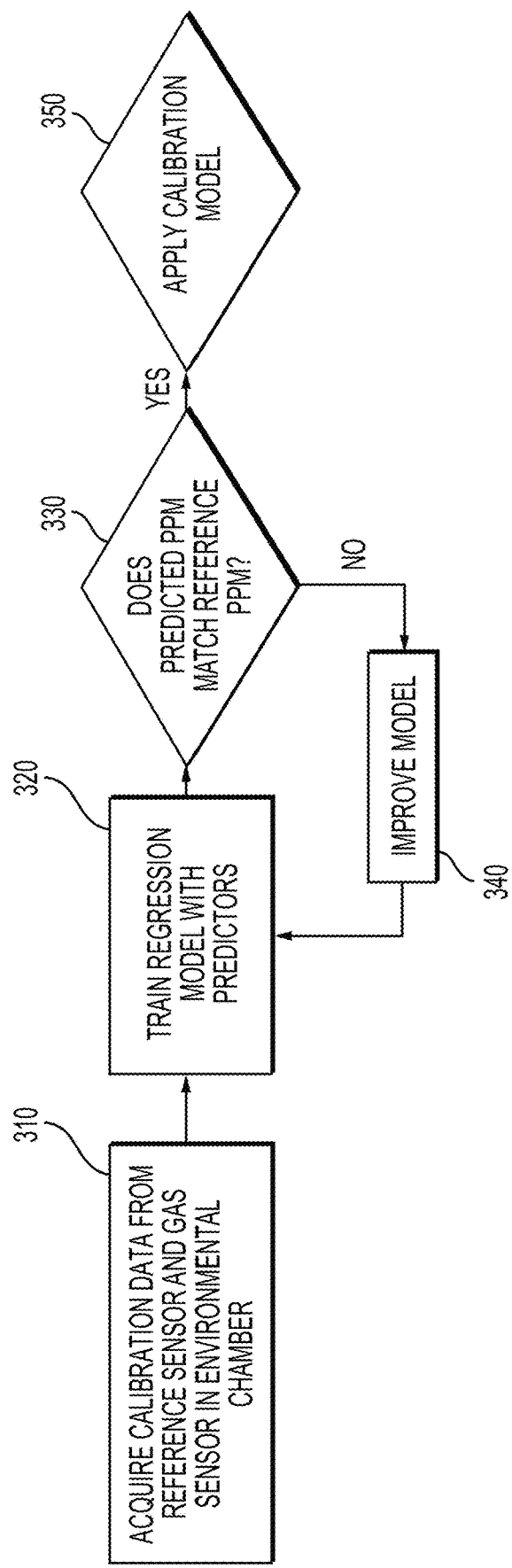
FIG. 3 is a flowchart of an example method for creating a calibration model for a methane sensor.

FIG. 3 is a flowchart of an example method for creating a calibration model for a methane sensor. At stage 310, the computing device 114 can acquire calibration data from a reference sensor and a gas sensor 108 an environmental chamber. The calibration data can include electrical resistance, temperature, RH, heater voltage, and methane in parts per million (ppm). The reference sensor and gas sensor 108 can collect the calibration data and send the data to the computing device 114 using any available communication protocol.

At stage 320, the computing device 114 can train a regression model with predictors for resistance, AH, and heater voltage. The computing device 114 can use data from gas sensor 108 in the environmental chamber to train the regression model. The AH can be calculated using the temperature and RH. In one example, the regression model can be a gaussian process regression model. A gaussian process regression model trained on predictors such as resistance, AH, heater voltage has significantly low mean average errors (MAE), thereby improving sensitivity of methane detection by the gas sensor 108.

At stage 330, the computing device 114 can determine whether the predicted methane ppm matches the reference ppm. To do this, the computing device 114 can input RH and T values from the environmental chamber sensor 108 into the regression model to obtain the predicted methane ppm. The computing device 114 can then compare the predicted methane ppm to the methane ppm measured by the reference sensor.

If the predicted and reference ppm do not match, then the method can proceed to stage 340 where the computing device 114 can modify the model based on the difference. For example, the computing device 114 can retrain the gaussian process regression model and again compare the predicted and reference methane ppm. The computing device 114 can continue to retrain the model until the methane ppm value match within a predetermined degree of variance.

If the predicted and reference ppm do match, then, at stage 350, the computing device 114 can use the calibration model to adjust methane readings from gas sensors 108. In one example, this can include transferring the calibration model to the gas sensor units 108. The gas sensor units 108 can then use the calibration model to adjust methane measurements reported to the computing device 114. Alternatively, the computing device 114 can locally store the calibration model and apply it to methane measurements received from the gas sensors 108.

Figure 4:
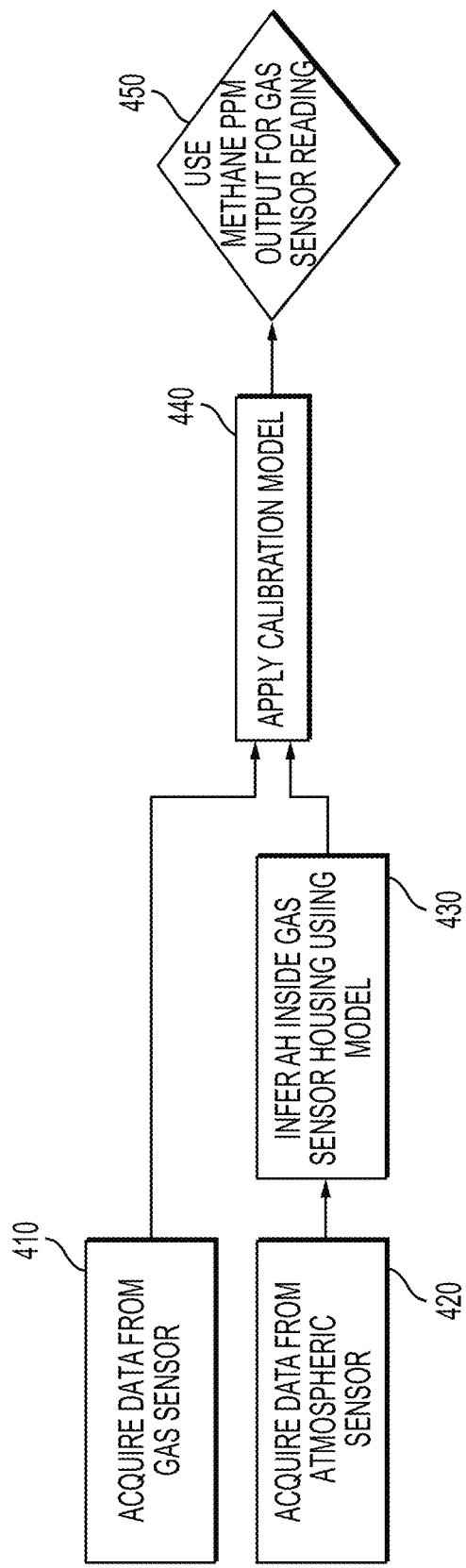
FIG. 4 is a flowchart of an example method for implementing a calibration model on methane sensor measurements.

FIG. 4 is a flowchart of an example method for implementing a calibration model on methane sensor measurements. At stage 410, the computing device 114 can acquire resistance and heater voltage data from a gas sensor 108. The gas sensor 108 can measure the resistance and heater voltage as it oxidizes the ambient methane. These measurements, when calibrated, can be used to determine the amount of ambient methane in the sensor housing 102.

At stage 420, the computing device 114 can acquire Te and RHe data from the external atmospheric sensor 112. For example, the external atmospheric sensor 112 can measure the Te and RHe and send the measurements to the computing device 114.

At stage 430, the computing device 114 can estimate the AHi inside the methane sensor device 100 using a calibration model. The computing device 114 can do this utilizing the method described previously regarding FIG. 2. In other words, the computing device 114 can calculate the AHi using the formulas in TABLE 1.

At stage 440, the computing device 114 can apply the calibration model. For example, the computing device 114 can receive methane measurements from the sensor 108 and the inferred AHi inside housing, apply the calibration model to this data, and report a correct methane ppm measurement after applying the model. In an example, the calibration model, the calibration model can be the calibration model described previously regarding FIG. 3. The calibration model can be a gaussian process regression model created to calibrate methane sensor readings.

At stage 450, the computing device 114 can use methane ppm output from applying the calibration model for gas sensor readings. For example, when the computing device 114 receives measurements from a gas sensor 108. If the methane sensor device 100 has an internal atmospheric sensor 110, then the computing device 114 can use the Ti and RHi measurements to apply the calibration model. If the methane sensor device 100 does not have an internal atmospheric sensor 110, then the computing device 114 can also receive Te and RHe measurements from the external atmospheric sensor 112. The computing device 114 can then cross-reference these measurements with the RHip and AHip arrays and apply the corresponding RHip and AHip values to the calibration model. The computing device 114 can then apply the calibration model to the gas sensor measurements to obtain a calibrated methane ppm count.

the computing device 114 can apply the calibration model to the measurements and use the resulting data as the measured ambient methane.

In an example, the states described in FIGS. 2, 3, and 4 can be performed consecutively to more accurately calculate ambient methane inside a closed housing with an absorbent filter. For example, a methane sensor device 100 that includes an internal atmospheric sensor 110 and an external atmospheric sensor 112 can be placed at a site. The computing device 114 can use measurements from the atmospheric sensors 110, 112 to calculate RHip and AHip using the method illustrated in FIG. 2. Then, using the method illustrated in FIG. 3, the computing device 114 can train a gaussian process regression model and improve the model by comparing RHip and AHip with measured RHi and AHi. After the model predicts the methane ppm within a predetermined degree of allowance, the model can be applied to live readings from methane sensors 100 in the field.

Other examples of the disclosure will be apparent to those skilled in the art from consideration of the specification and practice of the examples disclosed herein. Though some of the described methods have been presented as a series of steps, it should be appreciated that one or more steps can occur simultaneously, in an overlapping fashion, or in a different order. The order of steps presented are only illustrative of the possibilities and those steps can be executed or performed in any suitable fashion. Moreover, the various features of the examples described here are not mutually exclusive. Rather any feature of any example described here can be incorporated into any other suitable example. It is intended that the specification and examples be considered as exemplary only, with a true scope and spirit of the disclosure being indicated by the following claims.

What is claimed is:

1. A method for calibrating methane measurements from a methane sensor device with a closed housing and an absorbent filter, comprising:
   receiving a plurality of external temperature and humidity measurements from an external atmospheric sensor, the plurality of external temperature and humidity measurements having been iteratively taken over a period of time;
   receiving a plurality of internal temperature and humidity measurements from an internal atmospheric sensor, the plurality of internal temperature and humidity measurements having been iteratively taken over the period of time;
   calculating, using the plurality of internal temperature and humidity measurements and the plurality of external temperature and humidity measurements, predicted internal relative and absolute humidity values;
   training a calibration model using additional external temperature and humidity measurements and the predicted internal relative and absolute humidity values;
   receiving a methane gas measurement from a methane gas sensor; and
   applying the calibration model to the methane gas measurement.

2. The method of claim 1, wherein the plurality of external temperature and humidity measurements correspond to temperature and humidity outside the methane sensor, and the plurality of internal temperature and humidity measurements correspond to temperature and humidity inside the methane sensor.

3. The method of claim 1, wherein applying the regression model to the methane gas measurement includes sending the model to the methane gas sensor, and the methane gas sensor applies to the model recorded methane measurements.

4. The method of claim 1, wherein the calibration model is a gaussian process regression model.

5. The method of claim 1, wherein the methane gas sensor is made of a metal oxide.

6. The method of claim 1, wherein the calibration model is trained using resistance, absolute humidity, and heater voltage predictors.

7. The method of claim 1, wherein the external atmospheric sensor is positioned outside the closed housing of the methane sensor device, and the internal atmospheric sensor is positioned inside the closed housing of the methane sensor device.

8. A non-transitory, computer-readable medium containing instructions that, when executed by a hardware-based processor, causes the processor to perform stages for calibrating methane measurements from a methane sensor device with a closed housing and an absorbent filter, the stages comprising:
   receiving a plurality of external temperature and humidity measurements from an external atmospheric sensor, the plurality of external temperature and humidity measurements having been iteratively taken over a period of time;
   receiving a plurality of internal temperature and humidity measurements from an internal atmospheric sensor, the plurality of internal temperature and humidity measurements having been iteratively taken over the period of time;
   calculating, using the plurality of internal temperature and humidity measurements and the plurality of external temperature and humidity measurements, predicted internal relative and absolute humidity values;
   training a calibration model using additional external temperature and humidity measurements and the predicted internal relative and absolute humidity values;
   receiving a methane gas measurement from a methane gas sensor positioned inside the methane sensor device; and
   applying the calibration model to the methane gas measurement.

9. The non-transitory, computer-readable medium of claim 8, wherein the plurality of external temperature and humidity measurements correspond to temperature and humidity outside the methane sensor, and the plurality of internal temperature and humidity measurements correspond to temperature and humidity inside the methane sensor.

10. The non-transitory, computer-readable medium of claim 8, wherein applying the regression model to the methane gas measurement includes sending the model to the methane gas sensor, and the methane gas sensor applies to the model recorded methane measurements.

11. The non-transitory, computer-readable medium of claim 8, wherein the calibration model is a gaussian process regression model.

12. The non-transitory, computer-readable medium of claim 8, wherein the methane gas sensor is made of a metal oxide.

13. The non-transitory, computer-readable medium of claim 8, wherein the calibration model is trained using resistance, absolute humidity, and heater voltage predictors.

14. The non-transitory, computer-readable medium of claim 8, wherein the external atmospheric sensor is positioned outside the closed housing of the methane sensor device, and the internal atmospheric sensor is positioned inside the closed housing of the methane sensor device.

15. A system for calibrating methane measurements from a methane sensor device, comprising:
   the methane sensor device, comprising:
      a closed housing having at least one opening;
      an absorbent filter adjacent the at least one opening;
      an internal atmospheric sensor positioned inside the closed housing;
      an external atmospheric sensor positioned outside the closed housing; and
      a methane gas sensor positioned inside the closed housing;
   a memory storage including a non-transitory, computer-readable medium comprising instructions; and
   a hardware-based processor that executes the instructions to carry out stages comprising:
      receiving a plurality of external temperature and humidity measurements from the external atmospheric sensor, the plurality of external temperature and humidity measurements having been iteratively taken over a period of time;
      receiving a plurality of internal temperature and humidity measurements from the internal atmospheric sensor, the plurality of internal temperature and humidity measurements having been iteratively taken over the period of time;

calculating, using the plurality of internal temperature and humidity measurements and the plurality of external temperature and humidity measurements, predicted internal relative and absolute humidity values;

training a calibration model using additional external temperature and humidity measurements and the predicted internal relative and absolute humidity values;

receiving a methane gas measurement from a methane gas sensor positioned inside the methane sensor device; and applying the calibration model to the methane gas measurement.

16. The system of claim 15, wherein the plurality of external temperature and humidity measurements correspond to temperature and humidity outside the methane sensor, and the plurality of internal temperature and humidity measurements correspond to temperature and humidity inside the methane sensor.

17. The system of claim 15, wherein applying the regression model to the methane gas measurement includes sending the model to the methane gas sensor, and the methane gas sensor applies to the model recorded methane measurements.

18. The system of claim 15, wherein the calibration model is a gaussian process regression model.

19. The system of claim 15, wherein the methane gas sensor is made of a metal oxide.

20. The system of claim 15, wherein the calibration model is trained using resistance, absolute humidity, and heater voltage predictors.

* * * * *